US010039450B2

(12) United States Patent
Tokuda et al.

(10) Patent No.: US 10,039,450 B2
(45) Date of Patent: Aug. 7, 2018

(54) OPHTHALMOLOGIC APPARATUS

(71) Applicant: KABUSHIKI KAISHA TOPCON, Tokyo (JP)

(72) Inventors: Kanichi Tokuda, Saitama (JP); Hiroyuki Otsuka, Kounosu (JP)

(73) Assignee: KABUSHIKI KAISHA TOPCON, Tokyo (JP)

( * ) Notice: Subject to any disclaimer, the term of this patent is extended or adjusted under 35 U.S.C. 154(b) by 48 days.

(21) Appl. No.: 14/921,960

(22) Filed: Oct. 23, 2015

(65) Prior Publication Data
US 2016/0120405 A1    May 5, 2016

(30) Foreign Application Priority Data

Oct. 29, 2014 (JP) .................................. 2014-220662

(51) Int. Cl.
*A61B 3/15* (2006.01)
*A61B 3/11* (2006.01)
(Continued)

(52) U.S. Cl.
CPC ............ *A61B 3/152* (2013.01); *A61B 3/0025* (2013.01); *A61B 3/0075* (2013.01); *A61B 3/112* (2013.01);
(Continued)

(58) Field of Classification Search
CPC ......... A61B 3/15; A61B 3/0058; A61B 3/154; A61B 3/152; A61B 3/0075; A61B 3/145; A61B 3/14; A61B 3/112; A61B 3/117; A61B 3/0025; A61B 3/12; A61B 3/00; A61B 3/0083; A61B 3/1208

USPC ....... 351/208, 205, 206, 210, 211, 212, 214, 351/221, 236, 246; 600/316, 318, 319, 600/425, 476
See application file for complete search history.

(56) References Cited

U.S. PATENT DOCUMENTS

| 4,400,070 A | 8/1983 | Isono |
| 2013/0250242 A1* | 9/2013 | Cheng ..................... A61B 3/14 351/207 |

FOREIGN PATENT DOCUMENTS

| JP | 2002200043 A | 7/2002 |
| JP | 2008-278914 A | 11/2008 |
| JP | 2009172154 A | 8/2009 |

OTHER PUBLICATIONS

English translation of JP 2009-172154, machine translated, Jan. 19, 2017.*

(Continued)

*Primary Examiner* — Jie Lei
(74) *Attorney, Agent, or Firm* — Procopio, Cory, Hargreaves & Savitch LLP

(57) ABSTRACT

An ophthalmologic apparatus of an embodiment includes a focusing indicator projector, a fundus imaging unit, a driver, and a focusing controller. The focusing indicator projector is configured to irradiate light fluxes for projecting a pair of focusing indicators onto a fundus of an eye. The fundus imaging unit is configured to capture an image of the fundus. The driver is configured to move an optical system including the focusing indicator projector, the fundus imaging unit, and a focusing lens. The focusing controller is configured to move the focusing lens based on projection images of the focusing indicators captured by the fundus imaging unit, wherein the projection images are captured along with movement of the optical system by the driver.

11 Claims, 8 Drawing Sheets

(51) Int. Cl.
*A61B 3/12* (2006.01)
*A61B 3/14* (2006.01)
*A61B 3/00* (2006.01)
*A61B 3/117* (2006.01)

(52) U.S. Cl.
CPC ................ *A61B 3/117* (2013.01); *A61B 3/12* (2013.01); *A61B 3/14* (2013.01); *A61B 3/145* (2013.01)

(56) References Cited

OTHER PUBLICATIONS

Extended EP Search Report EP15191808.3, dated Mar. 29, 2016, 7 pages.

\* cited by examiner

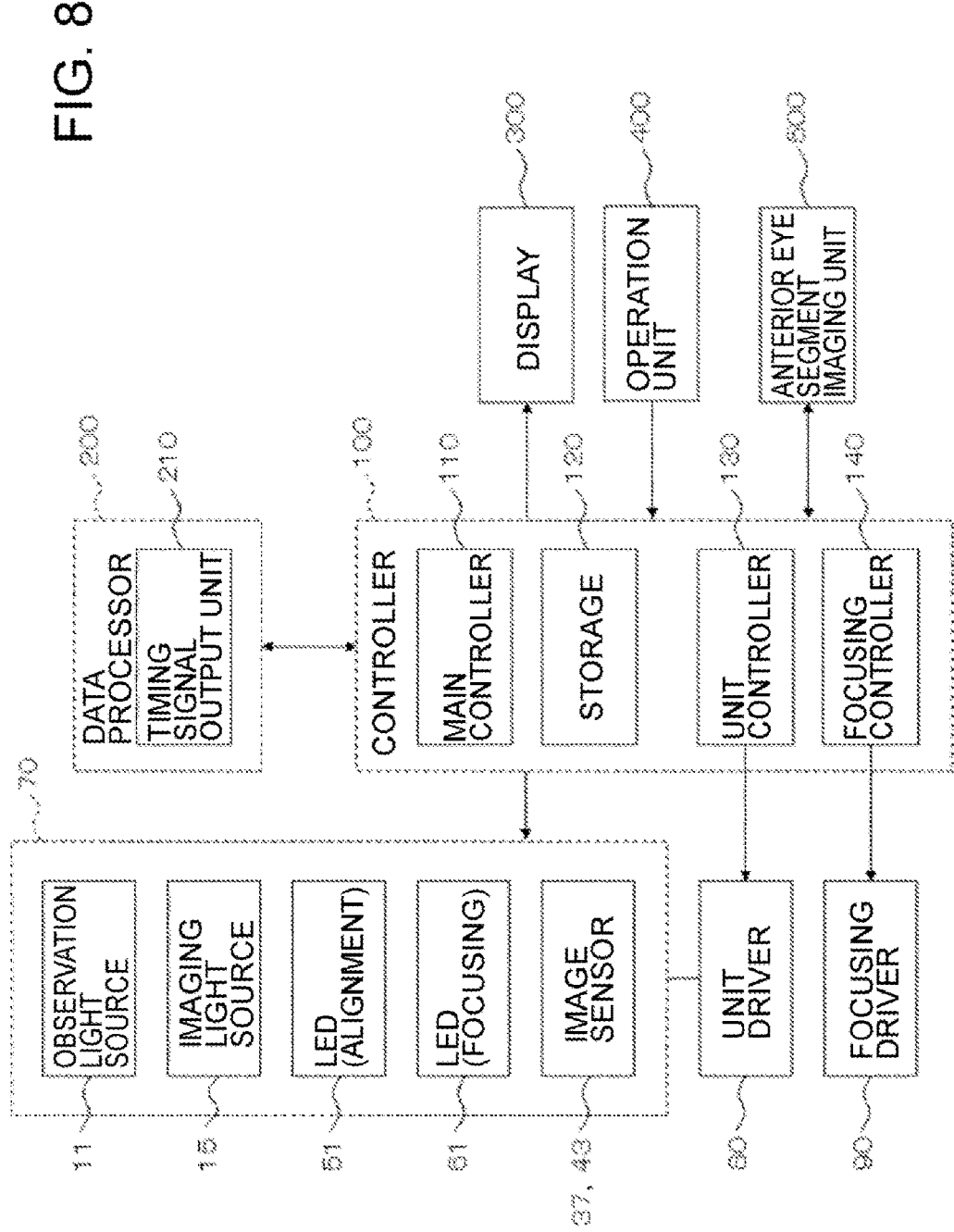

OPHTHALMOLOGIC APPARATUS

CROSS-REFERENCE TO RELATED APPLICATION

This application is based upon and claims the benefit of priority from Japanese Patent Application No. 2014-220662, filed 29 Oct. 2014; the entire contents of which are incorporated herein by reference.

FIELD

Embodiments described herein relate generally to an ophthalmologic apparatus.

BACKGROUND

The term "ophthalmologic apparatus" collectively means equipments used in the ophthalmology field. Examples of the ophthalmologic apparatus include an ophthalmologic imaging apparatus for imaging a subject's eye, an ophthalmologic examination apparatus for optically examining a subject's eye, and an ophthalmologic treatment apparatus for treating a subject's eye. Typical examples of the ophthalmologic imaging apparatus include a fundus camera, an optical coherence tomography (OCT) apparatus, a scanning laser ophthalmoscope (SLO), a slit lamp microscope, a surgical microscope, and the like. Typical examples of the ophthalmologic examination apparatus include a refractometer, a keratometer, a corneal topographer, a visual field test equipment, a wave-front analyzer, a specular microscope, a subjective eye examination apparatus, a tonometer, and the like. Typical examples of the ophthalmologic treatment apparatus include a laser therapy equipment, a cataract surgical equipment, a vitreous body surgical equipment, and the like.

Some ophthalmologic apparatuses perform the focusing of the optical system on a subject's eye. For example, to capture an image of the fundus of the eye, the ophthalmologic apparatus performs focusing on the fundus. The focusing is performed manually or automatically. In any case, an indicator (focusing indicator) is used to figure out the current focus state. As a typical example of the focusing indicator may be cited a split indicator. The split indicator is formed of a pair of light fluxes projected on the fundus, and a positional relationship between projection images of them indicates the current focus state. A user or the ophthalmologic apparatus moves a focusing lens such that two projection images are in a predetermined positional relationship to adjust the focus of the optical system on the fundus.

The focusing with the use of such a focusing indicator requires that both the projection images be recognizable. However, if the subject's eye has a small pupil, light fluxes projected toward the fundus and those reflected from the fundus are blocked by the iris, and the requirement may not be fulfilled. For example, Japanese Unexamined Patent Application Publication No. 2008-278914 discloses a method of automatic focusing for the case where one of the projection images cannot be detected. According to the method, the position of a split indicator (projection image) with respect to a fundus image is stored in advance, and focusing is performed such that one of split indicators, which is recognizable, is located in the stored position.

The conventional automatic focusing method is applicable when at least one of the indicators is recognizable. However, if both the indicators cannot be detected, manual focusing is required. Especially, when the pupil diameter is very small (e.g., 3.5 mm or less), any indicator is likely to be not recognizable.

SUMMARY

A purpose of the present invention is to improve automatic focusing for an eye with a small pupil.

An ophthalmologic apparatus of an embodiment includes a focusing indicator projector, a fundus imaging unit, a driver, and a focusing controller. The focusing indicator projector is configured to irradiate light fluxes for projecting a pair of focusing indicators onto a fundus of an eye. The fundus imaging unit is configured to capture an image of the fundus. The driver is configured to move an optical system including the focusing indicator projector, the fundus imaging unit, and a focusing lens. The focusing controller is configured to move the focusing lens based on projection images of the focusing indicators captured by the fundus imaging unit, wherein the projection images are captured along with movement of the optical system by the driver.

According to the embodiment, automatic focusing can be improved for eyes with a small pupil.

BRIEF DESCRIPTION OF THE DRAWINGS

FIG. 8 is a schematic diagram illustrating an example of the configuration of the ophthalmologic apparatus of the embodiment.

DETAILED DESCRIPTION

Embodiments of an ophthalmologic apparatus are described below. While the embodiments are particularly described as being applied to a fundus camera, the application of the embodiments is not limited to the fundus camera.

The embodiments are applicable to at least any ophthalmologic apparatuses with a configuration to project a focusing indicator on the fundus of the eye. For example, the embodiments are applicable to any ophthalmologic apparatuses used to image the fundus such as OCT, SLO, and slit lamp microscope. Further, the embodiments are applicable to any ophthalmologic examination apparatuses such as a visual field test equipment that applies light stimulation to a retina, and any ophthalmologic treatment apparatuses such as a laser therapy equipment used for photocoagulation of a retina.

The embodiments and their modifications may be combined arbitrarily.

First Embodiment

[Configuration]

Figure 1:
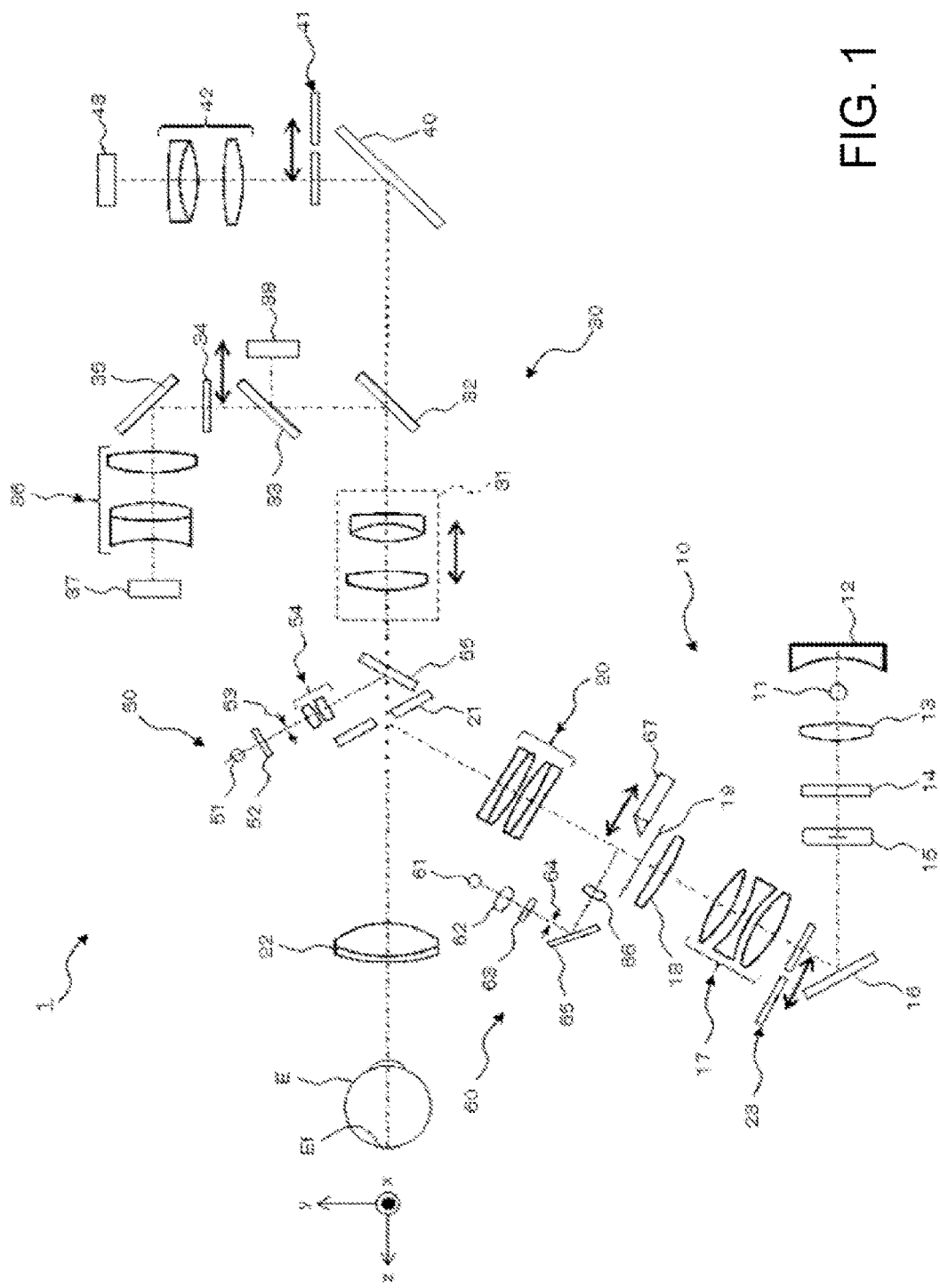
FIG. 1 is a schematic diagram illustrating an example of the configuration of an ophthalmologic apparatus according to an embodiment.
Figure 2:
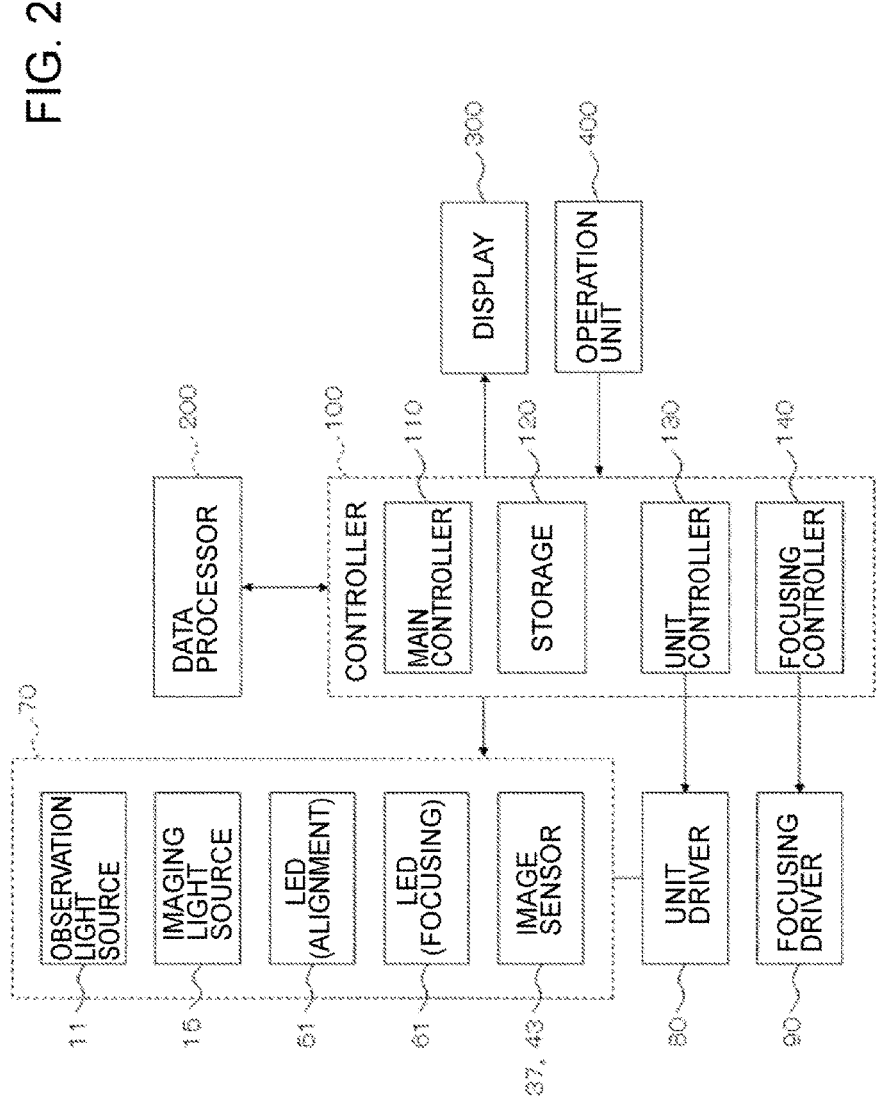
FIG. 2 is a schematic diagram illustrating an example of the configuration of the ophthalmologic apparatus of the embodiment.

With reference to FIGS. 1 and 2, a description is given of the configuration of an ophthalmologic apparatus according to an embodiment. FIG. 1 illustrates an example of the configuration of the optical system of an ophthalmologic apparatus 1. FIG. 2 illustrates an example of the configuration of the control system of the ophthalmologic apparatus 1.

The ophthalmologic apparatus 1 is provided with an optical system for forming a two-dimensional image (fundus image) representing the surface morphology of the fundus Ef of an eye E. Fundus images include observation images, photographic images, and the like. The observation image is a moving image of the fundus Ef captured by using near-infrared light. The photographic image is a still image of the fundus Ef captured by flashing light. Examples of the photographic image include a color image, a fluorescein angiography image, an indocyanine green fluorescent image, and an autofluorescent image. The ophthalmologic apparatus 1 may be capable of photographing an anterior eye segment Ea of the eye E.

As with conventional fundus cameras, the ophthalmologic apparatus 1 is provided with a jaw holder and a forehead rest for supporting the face of a subject. The ophthalmologic apparatus 1 is also provided with an illumination optical system 10 and an imaging optical system 30. The illumination optical system 10 irradiates the fundus Ef with illumination light. The imaging optical system 30 guides the illumination light reflected from the fundus to imaging devices (image sensors 37 and 43).

(Optical System)

The illumination optical system 10 includes an observation light source 11 that is a stationary light source capable of outputting stationary light (continuous light). The stationary light source may be capable of outputting flash light. The observation light source 11 includes, for example, a halogen lamp or a light emitting diode (LED). The light output from the observation light source 11 (observation illumination light) is reflected by a reflection mirror 12 having a curved reflective surface, and becomes near-infrared light after passing through a visible cut filter 14 via a condenser lens 13. Further, the observation illumination light is once converged near an imaging light source 15, reflected by a mirror 16, and passes through relay lenses 17 and 18, a diaphragm 19, and a relay lens 20. Then, the observation illumination light is reflected on the peripheral of an aperture mirror 21 (the region surrounding an aperture), passes through an objective lens 22, thereby illuminating the fundus Ef. An optical filter unit 23 is described later.

The observation illumination light reflected from the fundus (fundus reflection light) is refracted by the objective lens 22, passes through the aperture formed in the center region of the aperture mirror 21, passes through a dichroic mirror 55, travels through a focusing lens 31, and reaches a dichroic mirror 32. Further, the fundus reflection light passes through the dichroic mirror 32, is reflected by a mirror 40, and forms an image on the light receiving surface of the image sensor 43 by a condenser lens 42. The image sensor 43 detects, for example, the fundus reflection light at regular time intervals. Then, the image sensor 43 generates an electrical signal (image signal, video signal), and outputs it. An optical filter unit 41 is described later. The image sensor 43 is formed of, for example, a CCD image sensor or a CMOS image sensor.

The imaging light source 15 outputs flash light (also referred to as strobe light). The imaging light source 15 may be capable of outputting stationary light. The imaging light source 15 includes, for example, a xenon lamp or an LED. The light output from the imaging light source 15 (imaging illumination light) is irradiated to the fundus Ef through a route as with the observation illumination light. The imaging illumination light reflected from the fundus is guided to the dichroic mirror 32 via the same route as that of the observation illumination light.

When the fundus reflection light is infrared light, it passes through the dichroic mirror 32 and is detected by the image sensor 43 as traveling through the same route as that of the observation illumination light. On the other hand, when the fundus reflection light is visible light, the fundus reflection light is reflected by a dichroic mirror 33, passes through the dichroic mirror 33, is reflected by a mirror 35, and is detected by the image sensor 37 via a condenser lens 36. An optical filter unit 34 is described later. The image sensor 37 is formed of, for example, a CCD image sensor or a CMOS image sensor.

Described below are the optical filter units 23, 34 and 41. The optical filter units 23, 34 and 41 are provided with optical filters for a variety of usage. Examples of the optical filters include those for fluorography and red-free imaging. Examples of the filter for fluorography include those for fundus autofluorescence (FAF) imaging, fluorescein angiography (FA) imaging, indocyanine green (ICG) fluorescence imaging, and the like. Note that the optical filters are not so limited, and may be any optical filter used in various types of imaging in the ophthalmology field. When the optical filter unit 23 (34, 41) includes a plurality of optical filters, an optical filter selected by the user or the ophthalmologic apparatus 1 is arranged on the optical path.

A liquid crystal display (LCD) 38 displays a fixation target or a visual target for measuring visual acuity. The fixation target is a visual target for fixating the eye E, and is used on the occasion of observing or photographing the fundus Ef. The visible light output from the LCD 38 is reflected by the dichroic mirror 33, reflected by the dichroic mirror 32, travels through the focusing lens 31 and the dichroic mirror 55, passes through the aperture of the aperture mirror 21, and is incident on the eye E via the objective lens 22, thereby projected onto the fundus Ef. Incidentally, an internal fixation target including LEDs or the like may be provided in place of the LCD 38.

Further, as with conventional fundus cameras, the ophthalmologic apparatus 1 is provided with an alignment optical system 50 and a focus optical system 60. The alignment optical system 50 generates an indicator (alignment indicator) for position matching (alignment) of the optical system with respect to the eye E. The focus optical system 60 generates an indicator (focusing indicator) for adjusting the focus with respect to the fundus Ef. In the present embodiment, a split indicator is used as the focusing indicator.

The light (alignment light) output from an LED 51 of the alignment optical system 50 travels through diaphragms 52 and 53 and a relay lens 54, is reflected by the dichroic mirror 55, passes through the aperture of the aperture mirror 21, and is projected onto the anterior eye segment Ea (cornea) of the eye E by the objective lens 22.

The alignment light reflected from the cornea (cornea reflection light) travels through the same optical path as that of the observation illumination light reflected from the fundus, and is projected onto the light receiving surface of the image sensor 43. An image (alignment indicator image) captured by the image sensor 43 is displayed together with the observation image. A user may perform alignment by the same operation as performed on a conventional fundus camera. The alignment may also be performed automatically by moving the optical system based on the analysis of the position of the alignment indicator image.

To perform focusing, the reflective surface of a reflection rod 67 is arranged in a slanted position on the optical path of the illumination optical system 10. The light (focus light) output from an LED 61 of the focus optical system 60 passes through a collimate lens 62, is split into two light fluxes by a split indicator plate 63, passes through a two-hole diaphragm 64, is reflected by a mirror 65, and is once converged by a condenser lens 66 and reflected on the reflective surface of the reflection rod 67. Further, the focus light travels through the relay lens 20, and is reflected by the aperture mirror 21, thereby forming an image on the fundus Ef by the objective lens 22.

The focus light reflected from the fundus passes through the same route as alignment light reflected from the cornea and is detected by the image sensor 43. An image (split indicator) captured by the image sensor 43 is displayed together with an observation image (also with an alignment indicator image). As in the conventional case, the ophthalmologic apparatus 1 analyzes the position of the split indicator image, and moves the focusing lens 31 and the like to perform focusing. The user may perform manual focusing while visually checking the split indicator image.

While the ophthalmologic apparatus 1 of the present embodiment includes two image sensors, at least one image sensor may suffice. The ophthalmologic apparatus 1 (fundus camera) of the present embodiment may be a mydriatic type or a non-mydriatic type.

(Control System)

The control system of the ophthalmologic apparatus 1 is described with reference to FIG. 2.

The control system of the ophthalmologic apparatus 1 includes a controller 100, a data processor 200, a display 300, and an operation unit 400. The optical system illustrated in FIG. 1 is housed in an optical unit 70. The ophthalmologic apparatus 1 further includes a unit driver 80 and a focusing driver 90. The unit driver 80 is configured to move the optical unit 70 three-dimensionally. The movements of the optical unit 70 may include at least parallel movement (translation) and may include rotation (revolution). The focusing driver 90 is configured to move the focusing lens 31 in the optical axis direction of the imaging optical system 30. Although not illustrated, the ophthalmologic apparatus 1 includes other driving mechanisms (e.g., mechanisms for driving the optical filter units 23, 34 and 41).

(Controller 100)

The controller 100 performs various types of controls and operations. The controller 100 includes a main controller 110, a storage 120, a unit controller 130, and a focusing controller 140. Incidentally, the unit controller 130 and the focusing controller 140 may be provided inside the main controller 110. Besides, the data processor 200 may implement part of the functions of the unit controller 130 and/or the focusing controller 140.

(Main Controller 110, Storage 120)

The main controller 110 controls each unit of the ophthalmologic apparatus 1. In particular, the main controller 110 controls the observation light source 11, the imaging light source 15, the optical filter units 23, 34 and 41, the image sensors 37 and 43, the LED 51 of the alignment optical system 50, the LED 61 of the focus optical system 60, the reflection rod 67, and the like. Further, the main controller 110 displays information on the display 300.

The storage 120 stores various types of information. For example, the storage stores a computer program to cause the data processor 200 to perform certain processing. In addition, the storage 120 stores information (image data) acquired through the examination of the eye E, information related to patients (electronic medical records, etc.), and the like.

The storage 120 stores in advance correspondence information that is referred to for control of focusing. The correspondence information includes the correspondence relationship between projection positions of the split indicator (deviation amounts of diopter, deviation amounts of focus) and positions of the focusing lens 31. That is, the correspondence relationship is already known among positions where a split indicator image is rendered, deviation amounts of diopter (the deviation amounts of focus), and positions of the focusing lens 31.

Next, automatic alignment and automatic focusing are described. In the present embodiment, the automatic alignment is performed in the conventional manner. The automatic focusing may also be performed in the conventional manner, but can be performed in a mode specific to the present embodiment.

Figure 3A:
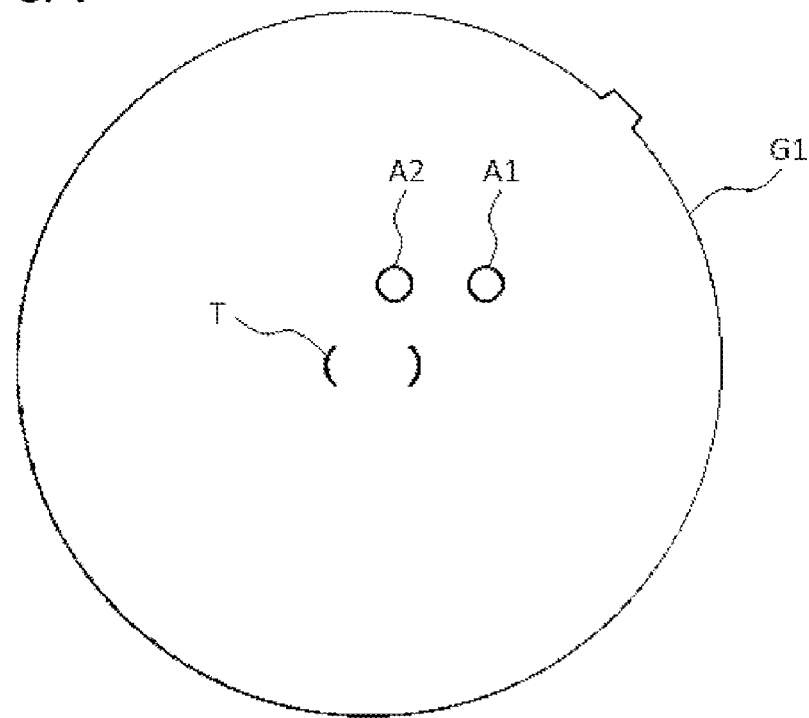
FIG. 3A is a schematic diagram illustrating an example of the operation of the ophthalmologic apparatus of the embodiment.
Figure 3B:
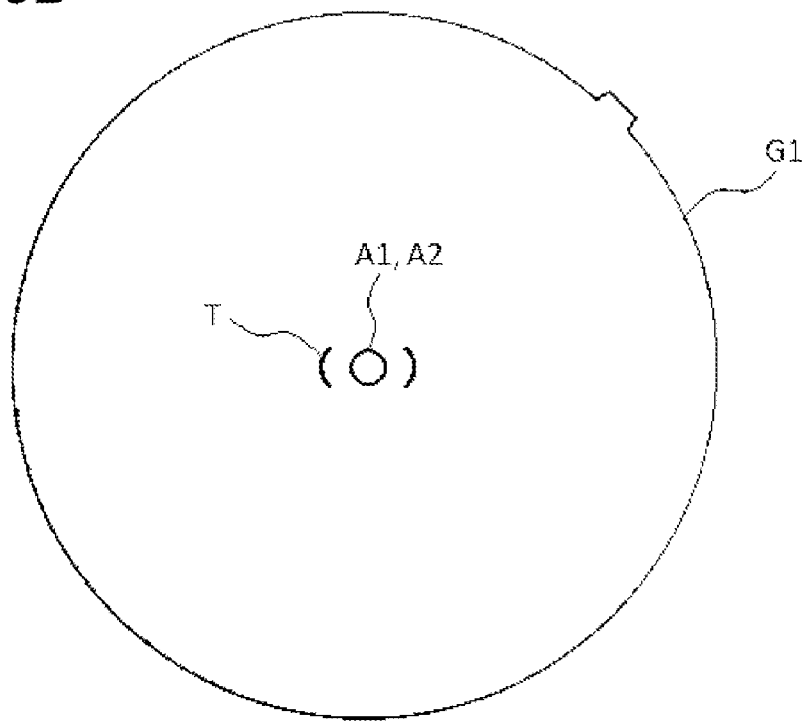
FIG. 3B is a schematic diagram illustrating an example of the operation of the ophthalmologic apparatus of the embodiment.

To perform alignment, a front image is captured of the anterior eye segment Ea where an alignment indicator is being projected. The front image is typically an infrared moving image. FIGS. 3A and 3B illustrate examples of alignment indicators rendered in the front image. In FIGS. 3A and 3B, the image of the anterior eye segment Ea is not illustrated. In a front image G1 in FIG. 3A, two images of alignment indicators (alignment indicator images) A1 and A2 are rendered as bright spots. Besides, the controller 100 displays a target image T in the form of a parenthesis indicating the target position of alignment in the center of the front image G1.

When the alignment to the eye E is unsuitable in the xy directions, the two alignment indicator images A1 and A2 are rendered in positions away from the target image T (see FIG. 3A). When the alignment is unsuitable in the z direction, the alignment indicator images A1 and A2 are rendered in different positions (see FIG. 3A). When the alignment is appropriate in all the xyz directions, the alignment indicator images A1 and A2 are rendered inside the target image T as being overlapped one upon the other (see FIG. 3B). The displacement (displacement amount, displacement direction) of the alignment indicator images A1 and A2 with respect to the target image T indicates the deviation (deviation amount, deviation direction) of alignment in the xy directions. The displacement (displacement amount, displacement direction) between the alignment indicator images A1 and A2 indicates the deviation (deviation amount, deviation direction) of alignment in the z direction.

The controller 100 (or the data processor 200) specifies (two) image areas corresponding to the alignment indicator images A1 and A2 based on pixel information (brightness values, etc.) of the front image G1. The controller 100 (or the data processor 200) specifies a characteristic position (center, center of gravity, etc.) in each image area, and obtains the displacement of each characteristic position with respect to the center of the target image T and the displacement between a pair of characteristic positions. Further, the controller 100 (or the data processor 200) obtains the deviation of alignment based on the displacement thus obtained, and obtains the amount of the movement of the optical system to eliminate the deviation. Then, the controller 100 controls the unit driver 80 to move the optical unit 70 by the amount thus obtained. This series of processes is repeated for each frame (or each some frames) of the front image G1 (infrared image). The automatic alignment is completed when the displacement becomes a predetermined threshold or less. After the completion of the automatic alignment, tracking may be started. Tracking is a function to adjust the position of the optical unit 70 such that a characteristic site of the eye E is rendered in a fixed position in frames.

Figure 4A:
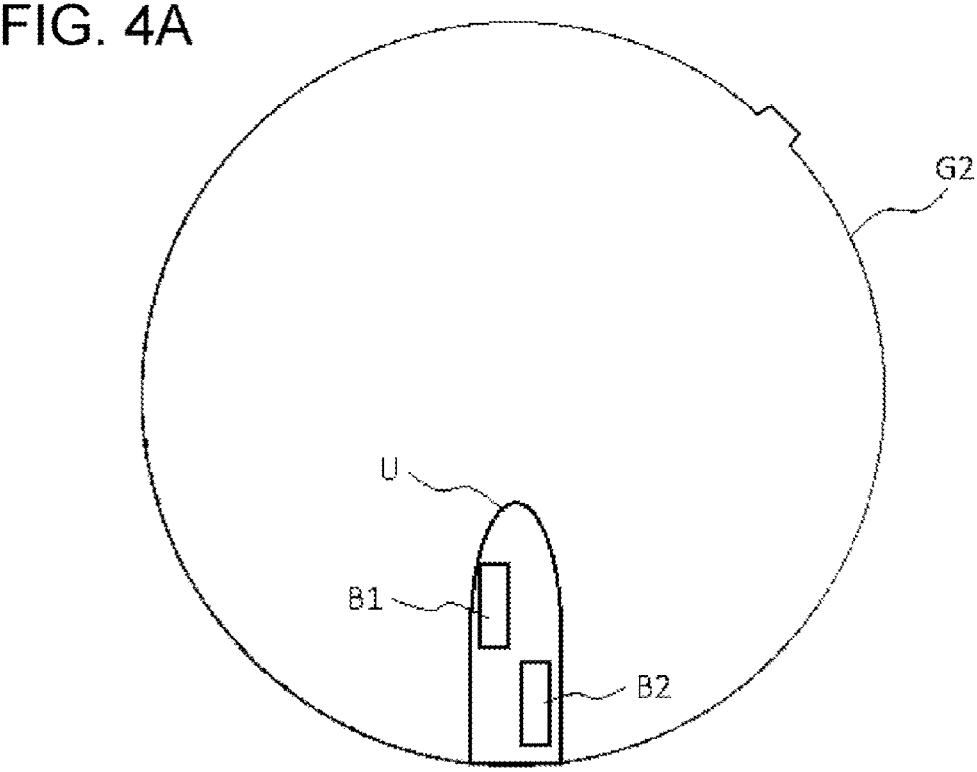
FIG. 4A is a schematic diagram illustrating an example of the operation of the ophthalmologic apparatus of the embodiment.
Figure 4B:
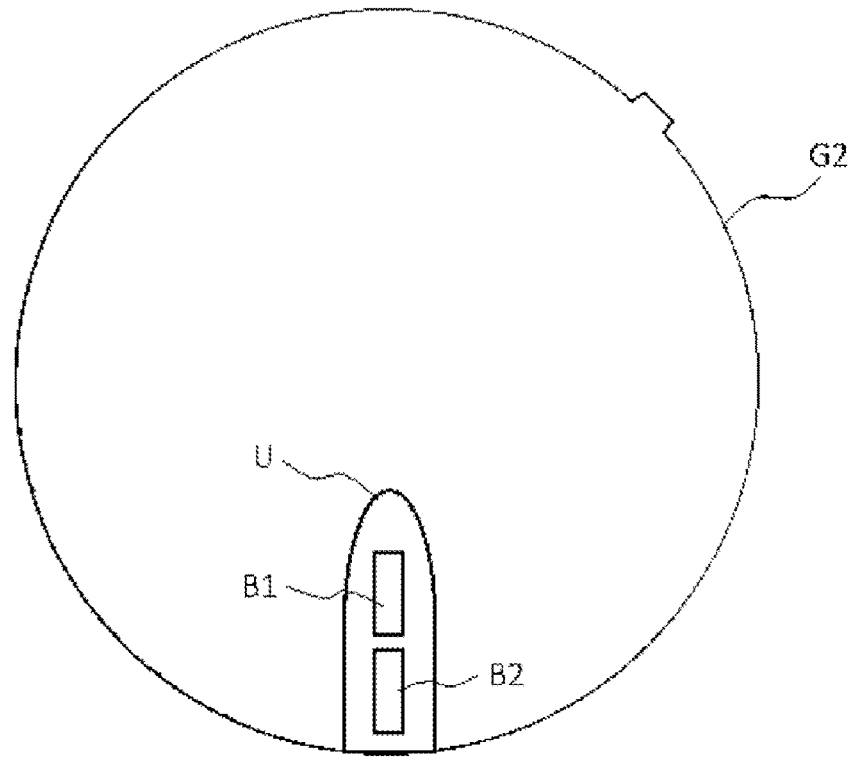
FIG. 4B is a schematic diagram illustrating an example of the operation of the ophthalmologic apparatus of the embodiment.

To perform automatic focusing, a front image is captured of the fundus Ef where the split indicator is being projected. The front image is typically an infrared moving image. FIGS. 4A and 4B illustrate examples of split indicators rendered in the front image. In FIGS. 4A and 4B, the image of the fundus Ef is not illustrated. In FIG. 4A, shadow U of the reflection rod 67 appears in a front image G2 of the fundus Ef, and two images of split indicators (split indicator images) B1 and B2 are rendered on the shadow U as bright lines.

When the focus position is unsuitable (in the z direction), i.e., when the focus position does not match the diopter of the eye E, the split indicator images B1 and B2 are rendered displaced each other in the horizontal direction. The displacement direction indicates the deviation direction of the focus position (+z direction or −z direction, i.e., increase in diopter (+D) or decrease in diopter (−D)), and the displacement amount indicates the size of the deviation of the focus position. When the focus position is appropriate, as illustrated in FIG. 4B, the split indicator images B1 and B2 are rendered aligned in the vertical direction.

The controller 100 (or the data processor 200) specifies (two) image areas corresponding to the split indicator images B1 and B2 based on pixel information (brightness values, etc.) of the front image G2. The controller 100 (or the data processor 200) specifies a characteristic position (center, center of gravity, axis line, etc.) in each image area, and obtains the displacement between a pair of characteristic positions. Further, the controller 100 (or the data processor 200) obtains the deviation of the focus position based on the displacement thus obtained, and obtains the amount of the movement of the focusing lens 31 to eliminate the deviation. The correspondence information is referred to in this process. That is, as in the conventional manner, the correspondence information associates the displacements (relative positions) between a pair of split indicator images with the positions of the focusing lens 31 in advance.

When both the split indicator images can be obtained as described above, the automatic focusing can be performed in a conventional manner. However, if there is a significant limitation in the optical route to the fundus Ef, such as the small pupil or the clouding of the eye E, either or both the split indicator images may not be detected. The method disclosed in Japanese Unexamined Patent Application Publication No. 2008-278914 can be applied to the case where one of the split indicator images cannot be detected. In this case, the correspondence information includes the same information as described in Japanese Unexamined Patent Application Publication No. 2008-278914. When none of the split indicator images can be detected, the ophthalmologic apparatus 1 moves the optical unit 70 to (sequentially) detect one or two split indicator image(s). For the split indicator image(s) thus detected, the deviation amount of diopter and the position of the focusing lens 31 (a position to which it is to be moved) can be obtained with reference to the correspondence information.

While the ophthalmologic apparatus 1 of the present embodiment is a fundus camera provided with a single focusing lens in the imaging optical system, it may be provided with two or more focusing lenses. For example, the apparatus disclosed in Japanese Unexamined Patent Application Publication No. 2014-113175 is provided with a focusing lens for the fundus camera function and a focusing lens for the OCT function. In such a case, as in the present embodiment, the position of the former focusing lens is obtained through the fundus camera function. Further, the position of the latter focusing lens can be obtained with reference to a predetermined correspondence relationship (correspondence information) between the focusing lenses.

(Unit Controller 130)

The unit controller 130 controls the unit driver 80. Thereby, the position of the optical unit 70 is three-dimensionally moved with respect to the eye E.

(Focusing Controller 140)

The focusing controller 140 controls the focusing driver 90 to change the focus position of the imaging optical system 30. Besides, the focusing controller 140 performs various processes related to focusing such as the process of the automatic focusing described above.

(Data Processor 200)

The data processor 200 performs various types of data processing. Specific examples of the processing performed by the data processor 200 are described later. Incidentally, the data processor 200 may function as part of the unit controller 130 or part of the focusing controller 140.

(Display 300, Operation Unit 400)

The display 300 and the operation unit 400 constitute a user interface for the ophthalmologic apparatus 1. The display 300 displays various types of information under the control of the main controller 110. The operation unit 400 is used to enter instructions and information. The operation unit 400 includes hardware such as an imaging trigger button and various switches. The main controller 110 controls the ophthalmologic apparatus 1 based on a signal from the operation unit 400. The display 300 may include a touch panel display. In this case, the user can provide instructions and information input by using a graphical user interface (GUI) displayed on the display 300.

[Operations]

Described below are operations of the ophthalmologic apparatus of the embodiment. Generally, the ophthalmologic apparatus performs preparations before imaging, examination or treatment as an original purpose. The preparations include the adjustment of the jaw holder and the forehead rest, alignment, focusing, tracking, the setting of the apparatus, the selection of an operation mode, and the like. In the following, the automatic focusing, which can be implemented by the present embodiment, is described. Other preparations, and imaging, examination, or treatment are performed in the conventional manner. In the preparations of the present embodiment, the automatic focusing is performed after alignment. A description is given of typical examples of the automatic focusing according to the embodiment.

First Operation Example

Figure 5:
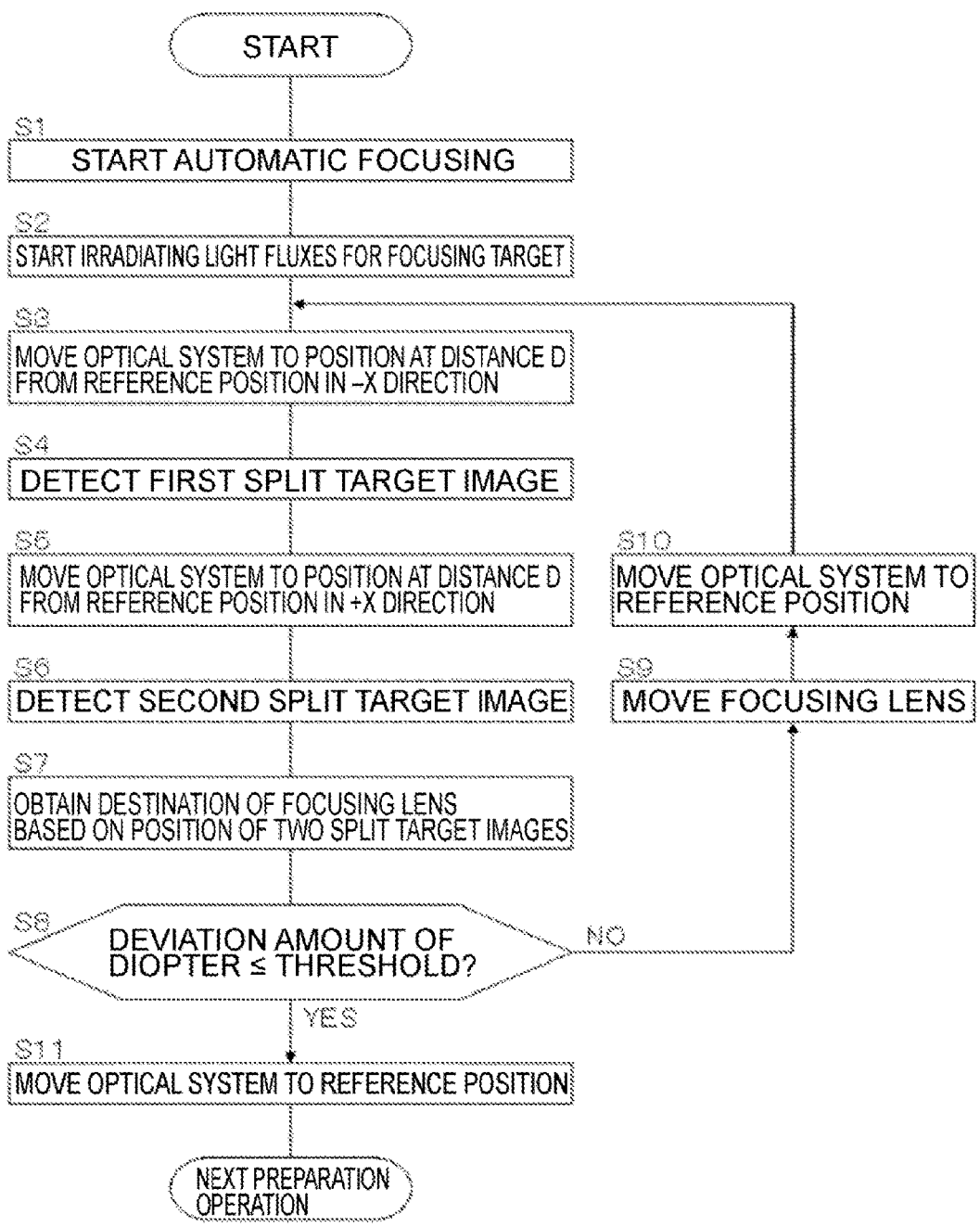
FIG. 5 is a flowchart of an example of the operation of the ophthalmologic apparatus of the embodiment.

In the first operation example, the optical unit 70 is moved by a predetermined distance in a predetermined direction from a position (reference position) determined by alignment to perform the automatic focusing. This operation example is described with reference to FIG. 5.

(S1: Start Automatic Focusing)

In response to the completion of preparations before the automatic focusing, the main controller 110 starts the automatic focusing. It is assumed herein that a fixation target has already been presented to the eye E. further, for example, in this step, the acquisition of an infrared moving image (observation image) of the fundus Ef starts.

(S2: Start Irradiating Light Fluxes for Focusing Indicators)

The main controller 110 turns on the LED 61 of the focus optical system 60 and also inserts the reflection rod 67 in the optical path of the illumination optical system 10. It is assumed herein that the eye E has a small pupil, and none of the split indicator images can be detected. More specifically, it is assumed that while the observation image of the eye E (and the shadow U of the reflection rod 67) can be obtained, both the split indicator images B1 and B2 as illustrated in FIG. 4A are not rendered in the observation image. The information acquired at this stage may be or may not be displayed on the display 300. Moreover, at this stage, the optical unit 70 is located in the reference position.

(S3: Move Optical System to Position at Distance d from Reference Position in −x Direction)

Next, the unit controller 130 controls the unit driver 80 to move the optical unit 70 by a distance d in the −x direction. The direction of the movement at this time is set in advance based on the direction of the arrangement of a pair of split indicator images. For example, differently from the present embodiment, if a pair of split indicator images is arranged in the horizontal direction, the movement direction of the optical unit 70 is set to (±) y direction.

The distance d may be a fixed value or individual values for subject's eyes, or may be a value selected according to the attributes of subjects (age, sex, injuries and diseases, the size of the eye ball, etc.). The fixed value is determined clinically or theoretically, for example. As one example, the fixed value may be 0.5 mm. The individual values for subject's eyes are values applied in the past or calculated from the attributes of individual eyes. In the case of the selected value, a plurality of values is prepared in advance to be selected according to the attributes of the subject's eye.

(S4: Detect First Split Indicator Image)

The focusing controller 140 (or the data processor 200) detects the first split indicator image acquired together with the observation image of the fundus Ef. In this example, as the optical unit 70 is moved in the −x direction in step S3, the upper split indicator image B1 is acquired.

(S5: Move Optical System to Position at Distance d from Reference Position in +x Direction)

Then, the unit controller 130 controls the unit driver 80 to move the optical unit 70 by the distance 2d in the +x direction. Thereby, the optical unit 70 is located in a position away from the reference position by the distance d in the +x direction.

(S6: Detect Second Split Indicator Image)

The focusing controller 140 (or the data processor 200) detects the second split indicator image acquired together with the observation image of the fundus Ef (the lower split indicator image B2).

(S7: Obtain Destination of Focusing Lens Based on Positions of Two Split Indicator Images)

The focusing controller 140 obtains the destination (movement amount) of the focusing lens 31 based on the positions of the first and second split indicator images with reference to the correspondence information.

(S8: Deviation Amount of Diopter≤Threshold?)

The focusing controller 140 determines whether the deviation amount of diopter (the deviation amount of focus), which corresponds to the destination of the focusing lens 31 obtained in step S7, is equal to or less than a predetermined threshold. The threshold is set to, for example, 0.3 diopter. If the deviation amount of diopter is equal to or less than the threshold (YES in step S8), the process moves to step S11. On the other hand, if the deviation amount of diopter exceeds the threshold (NO in step S8), the process moves to step S9.

(S9: Move Focusing Lens)

Having determined that the deviation exceeds the threshold (NO) in step S8, the focusing controller 140 controls the focusing driver 90 to move the focusing lens 31 to the destination obtained in step S7.

(S10: Move Optical System to Reference Position)

After step S9, the unit controller 130 controls the unit driver 80 to move the optical unit 70 to the reference position. Then, the process loops back to step S3, and a series of processes (steps S3 to S8) is performed again. That is, until it is determined that the deviation becomes the threshold or less (YES) in step S8, steps S3 to S10 are repeated. Incidentally, predetermined control may be performed when the number of the repetitions reaches a predetermined value. For example, the main controller 110 may display, on the display 300, a message informing the user of the failure of the automatic focusing, of transition to a manual focusing mode.

(S11: Move Optical System to Reference Position)

When it is determined that the deviation becomes the threshold or less (YES) in step S8, the unit controller 130 controls the unit driver 80 to move the optical unit 70 to the reference position. After that, the process moves to the next preparation operation. At this stage, various settings can be made. For example, the main controller 110 sets a flag to change the setting of the diaphragm(s) of the illumination optical system 10 and/or the imaging optical system 30 to the setting for the small pupil at the time of photographing.

Second Operation Example

Figure 6:
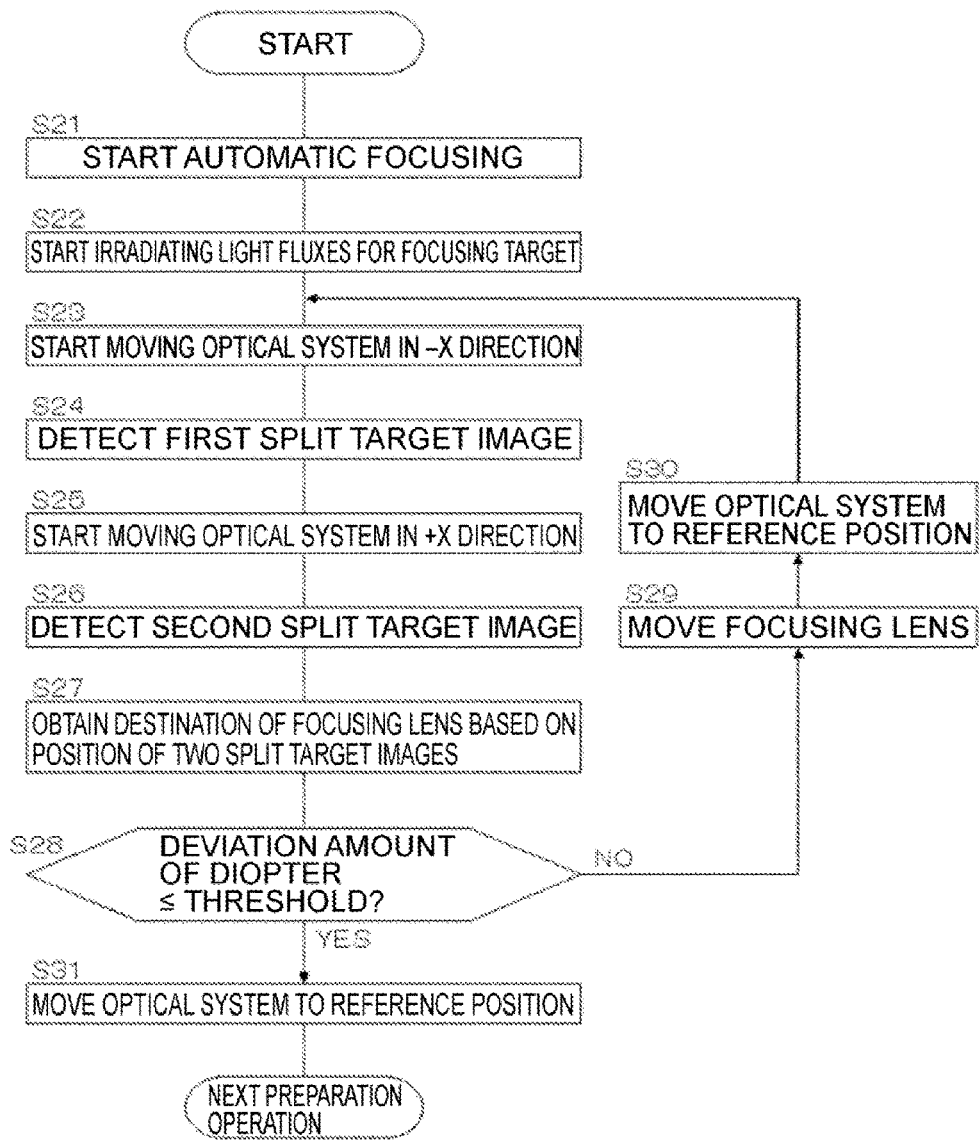
FIG. 6 is a flowchart of an example of the operation of the ophthalmologic apparatus of the embodiment.
Figure 7:
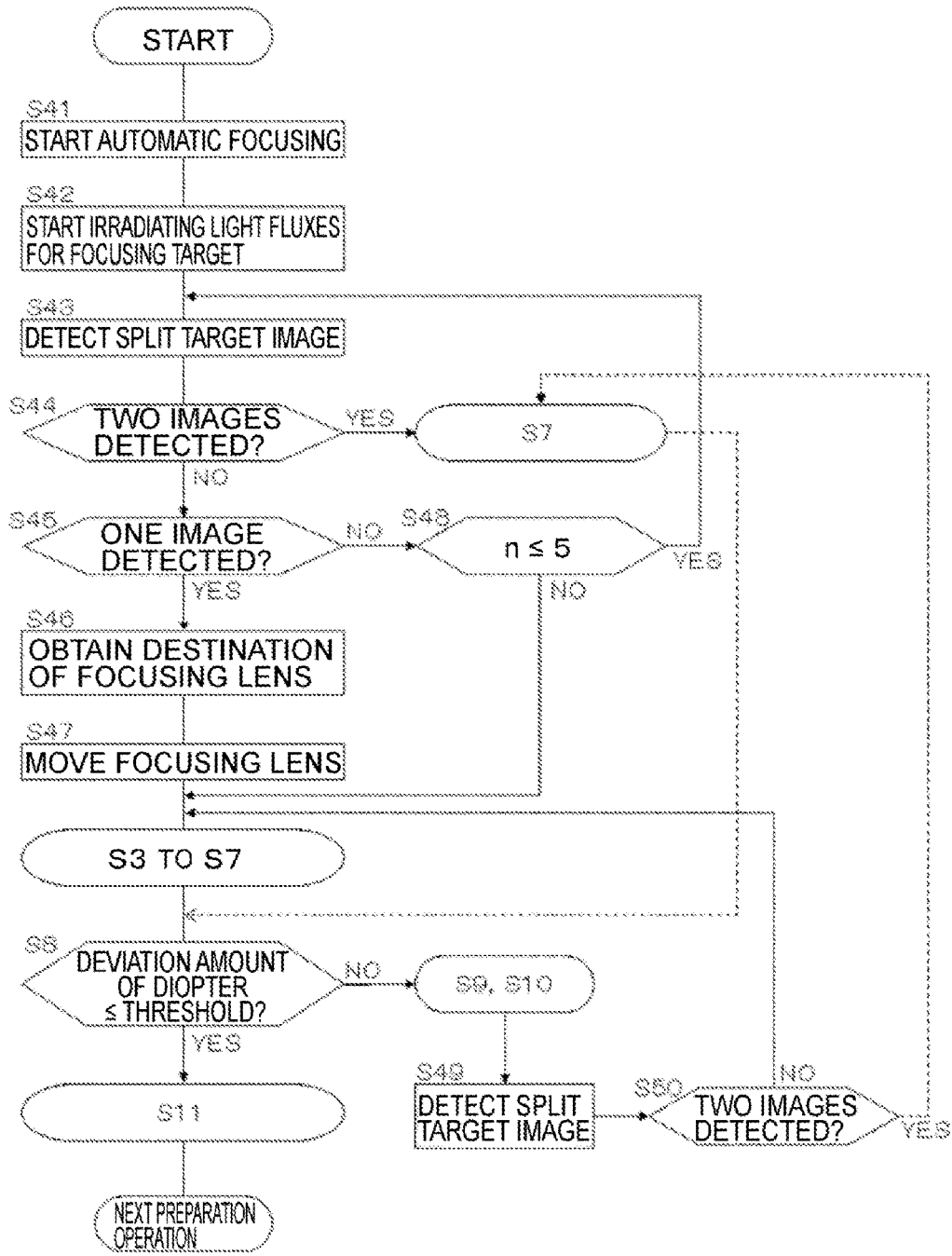
FIG. 7 is a flowchart of an example of the operation of the ophthalmologic apparatus of the embodiment.

In the second operation example, the split indicator images are detected while the optical unit 70 is being moved. This operation example is described with reference to FIG. 6.

(S21: Start Automatic Focusing)

This step is the same as step S1 in the first operation example.

(S22: Start Irradiating Light Fluxes for Focusing Indicators)

This step is the same as step S2 in the first operation example.

(S23: Start Moving Optical System in −x Direction)

Next, the unit controller 130 controls the unit driver 80 to start moving the optical unit 70 in the −x direction. This movement direction may be set in the same manner as in step S3 of the first operation example. The maximum movement distance in the −x direction may also be set. The maximum movement distance may be a fixed value or individual values for subject's eyes, or may be a value selected according to the attributes of subjects.

(S24: Detect First Split Indicator Image)

In parallel with the movement of the optical unit 70, the focusing controller 140 (or the data processor 200) detects the first split indicator image (the upper split indicator image B1) by analyzing the observation image of the fundus Ef.

(S25: Start Moving Optical System in +x Direction)

In response to the detection of the first split indicator image, the unit controller 130 controls the unit driver 80 to start moving the optical unit 70 in the +x direction.

(S26: Detect Second Split Indicator Image)

In parallel with the movement of the optical unit 70, the focusing controller 140 (or the data processor 200) analyzes the observation image of the fundus Ef. After the optical unit 70 reaches the reference position, the focusing controller 140 (or the data processor 200) detects the second split indicator image (the lower split indicator image B2).

(S27: Obtain Destination of Focusing Lens Based on Positions of Two Split Indicator Images)

This step is the same as step S7 in the first operation example.

(S28: Deviation Amount of Diopter≤Threshold?)

This step is the same as step S8 in the first operation example.

(S29: Move Focusing Lens)

This step is the same as step S9 in the first operation example.

(S30: Move Optical System to Reference Position)

This step is the same as step S10 in the first operation example.

(S31: Move Optical System to Reference Position)

This step is the same as step S11 in the first operation example.

Third Operation Example

In the third operation example, the focusing mode is switched according to the number of split indicator images rendered in the observation image of the fundus Ef. The third operation example contains some steps of the first operation example. The steps (steps S3 to S10) of the first operation example may be replaced by corresponding steps (steps S23 to S30) of the second operation example. Further, corresponding steps of other embodiments or modifications may also be applicable.

(S41: Start Automatic Focusing)

This step is the same as step S1 in the first operation example.

(S42: Start Irradiating Light Fluxes for Focusing Indicators)

This step is the same as step S2 in the first operation example.

(S43: Detect Split Indicator Image)

The focusing controller 140 (or the data processor 200) detects the split indicator image(s) acquired together with the observation image of the fundus Ef.

(S44: Two Images Detected?)

Having detected two split indicator images in step S43 (YES in step S44), the focusing controller 140 obtains the destination (movement amount) of the focusing lens 31 based on the positions of the two split indicator images with reference to the correspondence information (S7). Then, the process moves to step S8.

(S45: One Image Detected?)

When one split indicator image is detected in step S43 (YES in step S45), the process moves to step S46.

(S46: Obtain Destination of Focusing Lens)

When one split indicator image is detected (YES in step S45), the focusing controller 140 obtains the destination of the focusing lens 31 based on the position of this split indicator image, for example, in the following manner. First, the focusing controller 140 stores the position of the one split indicator image detected. Next, the focusing controller 140 sends an instruction to the unit controller 130. In response to the instruction, the unit controller 130 controls the unit driver 80 to move the optical unit 70. The distance and direction of the movement at this time may be set as default, or may be derived from the position of the one split indicator image detected. Alternatively, the optical unit 70 may be moved by analyzing a fundus image in real time and monitoring the rendering state of the split indicator images. The focusing controller 140 obtains the position of the other split indicator image rendered in the fundus image in this manner. The focusing controller 140 then obtains the destination of the focusing lens 31 (diopter value) based on the positions of both the split indicator images (and the movement amount and movement direction of the optical unit 70 when the position of the other split indicator image is acquired). Here, by correcting the deviation of the focus position due to lenses using a quadratic equation, known processing can be performed for correcting the destination obtained as above.

(S47: Move Focusing Lens)

The focusing controller 140 controls the focusing driver 90 to move the focusing lens 31 to the destination obtained in step S46. After the movement of the focusing lens 31, steps S3 to S8 of the first operation example are performed.

(S48: n≤5?)

When no split indicator image is detected in step S45 (NO in step S45), the process moves to step S48. In step S48, the focusing controller 140 counts the number n of times that no split indicator image is detected. When the number n is a predetermined number (e.g., 5) or less (YES in step S48), the process returns to step S43.

On the other hand, when the number n exceeds the predetermined number (NO in step S48), steps S3 to S8 of the first operation example are performed.

(S8: Deviation Amount of Diopter≤Threshold?)

The focusing controller 140 determines whether the deviation amount of diopter (the deviation amount of focus), which corresponds to the destination of the focusing lens 31 obtained in step S7, is equal to or less than a predetermined threshold. If the deviation amount of diopter is equal to or less than the threshold (YES in step S8), the optical system is moved to the reference position (S11). Thereafter, the process moves to the next preparation.

(S49: Detect Split Indicator Image)

On the other hand, if the deviation amount of diopter exceeds the threshold (NO in step S8), steps S9 and S10 of the first operation example are performed. Subsequently, the focusing controller 140 (or the data processor 200) detects the split indicator image(s) acquired together with the observation image of the fundus Ef.

(S50: Two Images Detected?)

When two split indicator images are detected in step S49 (YES in step S50), step S7 of the first operation example is performed. Then, the process moves to step S8.

On the other hand, when two split indicator images are not detected in step S49 (NO in step S50), steps S3 to S8 of the first operation example are performed again. This loop is repeated until "YES" is obtained in step 8, or it may be repeated a predetermined number of times.

Fourth Operation Example

In the first to third operation examples, after the split indicator images are detected by moving the optical system and the focusing lens is moved, the optical system is moved to a predetermined position (reference position) (incidentally, this process may be dispensed with when the movement amount of the optical system is small). This is to prevent flare from in a photographic image. However, considering that the eye E has a small pupil, a light flux for illuminating the fundus Ef (ring illumination light) may not suitably irradiate the fundus Ef. The forth operation example describes the process to avoid such a situation. Incidentally, a second embodiment describes another example to achieve this.

In the fourth operation example, the optical system is moved to a predetermined position through the monitoring of the projection state of split indicators. The storage 120 stores, in advance, conditions to move the optical system to the predetermined position. Examples of the conditions include that one or two split indicator images be detected, that the split indicator image(s) be rendered in a predetermined area or that the area (size) of the split indicator image(s) detected be the largest, and the like.

The focusing controller 140 (or the data processor 200) detects a split indicator image by analyzing the observation image of the fundus Ef. This process is performed while the optical system is kept still or is being moved. Note that there are cases in which the pupil of the eye E may gradually expand with the lapse of time.

When detecting a split indicator image while the optical system is kept still, the unit controller 130 moves the optical system to the predetermined position in response to that the split indicator image thus detected satisfies predetermine conditions along with the expansion of the pupil.

On the other hand, when detecting a split indicator image while the optical system is being moved, the unit controller 130 moves the optical system to the predetermined position in response to that the split indicator image thus detected satisfies predetermined conditions along with the expansion of the pupil and/or the movement of the optical system. In this case, the predetermined position may be a reference position determined by alignment in the earlier process or the position of the optical system when the split indicator image satisfies the predetermined conditions.

[Actions and Effects]

Actions and effects of the ophthalmologic apparatus of the present embodiment are described.

According to the embodiment, the ophthalmologic apparatus includes a focusing indicator projector (the focus optical system 60), a fundus imaging unit (the illumination optical system 10 and the imaging optical system 30), a driver (the unit driver 80), and a focusing controller (the focusing controller 140 (and the data processor 200)). The focusing indicator projector is configured to irradiate light fluxes for projecting a pair of focusing indicators onto a fundus of an eye. The fundus imaging unit is configured to capture an image of the fundus of the eye. The driver is configured to move an optical system including the focusing indicator projector, the fundus imaging unit, and a focusing lens (31). The focusing controller is configured to move the focusing lens based on projection images of the focusing indicators (split indicator images) captured by the fundus imaging unit, wherein the projection images are acquired by the movement of the optical system by means of the driver.

With the ophthalmologic apparatus thus configured, even if the projection image(s) of a focusing indicator(s) is (are) not detected, the projection image(s) can be detected by moving the optical system and automatic focusing can be performed based on the projection image(s) detected. Thus, an improvement can be achieved in automatic focusing for the eye with a small pupil.

In the present embodiment, the ophthalmologic apparatus may further include an alignment indicator projector (the alignment optical system 50) configured to project an alignment indicator onto the eye. In this case, the driver can move the optical system by a predetermined distance in a predetermined direction from a reference position determined based on the alignment indicator. In addition, the focusing controller can move the focusing lens based on the projection images of the focusing indicators captured by the fundus imaging unit after the driver moves the optical system.

With this configuration, the optical system can be moved with reference to a suitable position determined by alignment. Thus, the projection images of the focusing indicators can be detected preferably (smoothly, swiftly, and easily).

In the present embodiment, after moving the optical system to a first position at a first distance away from the reference position in a first direction, the driver can move the optical system to a second position at a second distance away from the reference position in a second direction. Besides, the focusing controller can move the focusing lens based on the projection image of the focusing indicator (first projection image) captured by the fundus imaging unit when the optical system is located in the first position, and the projection image of the focusing indicator (second projection image) captured by the fundus imaging unit when the optical system is located in the second position.

Here, the second direction may be opposite to the first direction with respect to the reference position and the second distance may be equal to the first distance. That is, it may be configured that the projection images of the focusing indicators are detected when the optical system is located in each of two positions symmetrical to each other with respect to the reference position.

With this configuration, automatic focusing can be performed based on two projection images captured when the optical system is located at different positions. That is, after the sequential detection of two projection images to be detected for automatic focusing, automatic focusing can be performed based on the projection images. Thus, the accuracy and precision of automatic focusing can be increased.

In the present embodiment, in parallel with the movement of the optical system by the driver, the fundus imaging unit can capture a moving image of the fundus of the eye being irradiated with the light fluxes from the focusing indicator projector. Further, the focusing controller can move the focusing lens based on the projection images of the focusing indicators rendered in the moving image captured by the fundus imaging unit.

With this configuration, differently from the above configuration in which the projection image of the focusing indicator is detected when the optical system is located in a predetermined position, automatic focusing can be performed by using the projection image detected according to the movement of the optical system. In other words, this configuration enables the search of the projection image of the focusing indicator while the optical system is being moved. Accordingly, the projection image is more likely to be detected. In other words, automatic focusing is more likely to be successful.

In the present embodiment, the focusing controller can move the focusing lens based on a first projection image and a second projection image of the focusing indicators rendered in the moving image. Here, it may be configured that the first projection image is acquired when the optical system is located in a first direction from an initial position, and the second projection image is acquired when the optical system is located in a second direction from the initial position. The initial position may be the reference position of the optical system determined by using the alignment indicator. The second direction may be opposite to the first direction with respect to the initial position.

With this configuration, it is possible to sequentially detect two projection images to be detected for automatic focusing, and perform automatic focusing based on the two images acquired. Thus, the accuracy and precision of automatic focusing can be increased.

In the present embodiment, when none of the projection images of the focusing indicators is rendered in the image of the fundus captured by the fundus imaging unit, the focusing controller may start moving the optical system to acquire the projection image of the focusing indicator.

Further, in the present embodiment, when one of the projection images of the focusing indicators is rendered in the image of the fundus captured by the fundus imaging unit, the focusing controller may start moving the optical system to acquire the projection image of the focusing indicator after moving the focusing lens based on the one projection image.

Still further, in the present embodiment, when projection images of both the focusing indicators are rendered in the image of the fundus captured by the fundus imaging unit, the focusing controller may move the focusing lens based on a positional relationship between the projection images.

With such configurations, according to the detection result of the projection image(s) of the focusing indicator(s), i.e., the number of projection images detected, focusing mode can be switched as appropriate.

In the present embodiment, after the focusing controller moves the focusing lens, the driver can move the optical system to a predetermined position. The predetermined position may be a reference position determined by alignment.

With this configuration, after the completion of the movement of the optical system for automatic focusing, the optical system can be automatically moved to a predetermined position. This enables preparation operations before imaging, measurement, or treatment to be performed smoothly without difficulty. In addition, it is possible to prevent flare from a photographic image, and also to prevent a light flux for measurement or treatment from vignetting by the iris.

In the present embodiment, the driver can move the optical system to a predetermined position after the projection images of the focusing indicators captured by the fundus imaging unit satisfies predetermined conditions.

With this configuration, the optical system can be moved to a predetermined position in response to the fact that the projection images can be suitably detected. Thus, a light flux for imaging, measurement, or treatment can be suitably guided to the fundus of the eye.

Second Embodiment

According to the second embodiment, an ophthalmologic apparatus is capable of photographing the anterior eye segment in parallel with the photographing of the fundus of the eye, and is configured to perform a variety of processing based on the image of the anterior eye segment obtained.

FIG. 8 illustrates an example of the configuration of the ophthalmologic apparatus according to the second embodiment. The ophthalmologic apparatus has the same optical configuration as described in the first embodiment unless otherwise specified.

The ophthalmologic apparatus includes an anterior eye segment imaging unit 500. The anterior eye segment imaging unit 500 photographs the anterior eye segment Ea of the eye E. In particular, the anterior eye segment imaging unit 500 is capable of capturing a moving image of the anterior eye segment Ea. The anterior eye segment imaging unit 500 includes, for example, at least one camera (video camera) provided on the front surface of the case of the optical unit 70 (the surface on the eye E side). If provided with two or more cameras, the ophthalmologic apparatus is capable of stereo photography of the anterior eye segment Ea. That is, if there are two or more cameras, the three-dimensional position of the optical system with respect to the eye E can be obtained based on two or more images captured substantially simultaneously with the two or more cameras, and further, alignment can be performed. As to this configuration, reference may be had to, for example, Japanese Unexamined Patent Application Publication No. 2013-248376, submitted by the applicant.

The data processor 200 includes a timing signal output unit 210. The timing signal output unit 210 outputs a timing signal for capturing the projection image of the focusing indicator on the fundus Ef. More specifically, the timing signal output unit 210 first analyzes a moving image (anterior segment projection image) obtained by photographing the anterior eye segment Ea with the anterior eye segment imaging unit 500. Thereby, the timing signal output unit 210 determines the rendering state of the projection image of the light fluxes from the focus optical system 60. When all light fluxes from the focus optical system 60 pass through the pupil and are projected onto the fundus Ef, a projection image is not rendered in the anterior segment projection image. On the other hand, when at least part of the light fluxes from the focus optical system 60 does not pass through the pupil, a projection image is rendered in the anterior segment projection image. In general, alignment is performed before automatic focusing. Therefore, such cases can be ignored where a projection image is not detected despite that at least part of the light fluxes does not pass through the pupil.

Examples of determination made by the timing signal output unit 210 include determination as to whether a projection image is rendered, determination as to whether either or both projection images are rendered, determination as to the size of the rendering area of a projection image, and comparison between the rendering area of the projection image and a predetermined threshold.

Further, based on the determination result of the rendering state of the projection image in an anterior segment moving image, the timing signal output unit 210 outputs a timing signal for capturing the projection image of the focusing indicator on the fundus Ef. For example, the timing signal output unit 210 outputs the timing signal when no projection image is rendered, when only one of projection images is rendered, when the rendering area of the projection image is smaller than a predetermined threshold, or the like. That is, the timing signal output unit 210 detects the fact that light fluxes from the focus optical system 60 are not improperly blocked by the iris and the focusing indicators are suitably formed on the fundus Ef, and thereby outputs the timing signal.

The controller 100 receives the timing signal output from the timing signal output unit 210. In response to the input of the timing signal, the focusing controller 140 (or the data processor 200) detects the projection image of the focusing indicator rendered in an image of the fundus Ef captured by the illumination optical system 10 and the imaging optical system 30. Further, based on the projection image detected, the focusing controller 140 controls the focusing driver 90 to move the focusing lens 31. Here, the focusing controller 140 (or the data processor 200) performs the same processing as in the first embodiment except the timing of processing.

According to the second embodiment, it is possible to detect the projection images of the focusing indicators at the timing when the focusing indicators are suitably projected onto the fundus Ef, and perform automatic focusing based on the projection images detected. As a result, automatic focusing is more likely to be successful.

Described below is an example of the operation of the ophthalmologic apparatus of the second embodiment. The ophthalmologic apparatus has the function of monitoring the size of the pupil of the eye E (monitoring unit). The pupil size may be, for example, the maximum diameter of the pupil, the average diameter of the pupil, the diameter of the pupil in a predetermined direction, the perimeter of the pupil, the area of an image region corresponding to the pupil, or the like.

The pupil size monitoring function may be implemented by, for example, the anterior eye segment imaging unit 500 and the data processor 200. The anterior eye segment imaging unit 500 captures an anterior segment moving image of the eye E. The data processor 200 analyzes the anterior segment moving image to specify the pupil area, and calculates the value that represents its size. Besides, the data processor 200 compares the value thus calculated with a predetermined threshold. When the value calculated is equal to or above the predetermined threshold, the data processor 200 sends a signal to the controller 100.

Having received the signal from the data processor 200, the unit controller 130 controls the unit driver 80 to move the optical unit 70 to a predetermined position. The predetermined position may be a reference position determined by alignment in the earlier process. Incidentally, the process of this operation example is performed in step S9 or step S29 of the first embodiment.

With this configuration, after the completion of the movement of the optical system for automatic focusing, the optical system can be automatically moved to a predetermined position. This enables preparation operations before imaging, measurement, or treatment to be performed smoothly without difficulty. In addition, it is possible to prevent flare from being incorporated into a photographic image, and also to prevent a light flux for measurement or treatment from vignetting by the iris. In addition, in response to the enlargement of the pupil of the eye E, i.e., in response to the fact that the projection images can be suitably detected in the fundus Ef, the optical system can be moved to a predetermined position. Thus, a light flux for imaging, measurement, or treatment can be suitably guided to the fundus Ef.

Described below is another example of the operation of the ophthalmologic apparatus of the second embodiment. The ophthalmologic apparatus has the function of measuring the size of the pupil of the eye (measurement unit). The pupil size may be, for example, the maximum diameter of the pupil, the average diameter of the pupil, the diameter of the pupil in a predetermined direction, the perimeter of the pupil, the area of an image region corresponding to the pupil, and the like.

For example, as with the pupil size monitoring function described above, the pupil size measurement function may be implemented by the anterior eye segment imaging unit 500 and the data processor 200. The data processor 200 determines whether the value that represents the pupil size is equal to or below a predetermined threshold. When the value is equal to or below the predetermined threshold, the data processor 200 sends a signal to the controller 100.

Having received the signal from the data processor 200, the unit controller 130 starts moving the optical system for acquiring the projection images of the focusing indicators on the fundus Ef (step S3, step S23).

With this configuration, in response to the enlargement of the pupil of the eye E, i.e., in response to the fact that the focusing indicators can be suitably projected onto the fundus Ef, the movement of the optical unit 70 can be started to capture the projection images of the focusing indicators. Thus, the detection of the focusing indicators is more likely to be successful. Accordingly, automatic focusing is more likely to be successful.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic apparatus comprising:
 a focusing indicator projector configured to irradiate light fluxes for projecting a pair of focusing indicators onto a fundus of an eye;
 a fundus imaging unit configured to capture an image of the fundus;
 a driver configured to move an optical system including the focusing indicator projector, the fundus imaging unit, and a focusing lens;
 a focusing controller configured to move the focusing lens based on projection images of the focusing indicators captured by the fundus imaging unit, wherein the projection images are captured along with movement of the optical system by the driver;
 a control system, which controls the driver; and
 a measurement unit configured to measure a size of a pupil of the eye,
 wherein the control system controls the driver to start moving the optical system for acquiring the projection images of the focusing indicators in response to the measured sized of the pupil obtained by the measurement unit being equal to or below a threshold,
 wherein the control system controls the driver to move the optical system to a predetermined position after the focusing controller moves the focusing lens,
 wherein the control system controls the driver to move the optical system from a reference position determined based on the pair of alignment indicators by a distance in a direction, and
 the control system controls the driver to move the optical system to a first position at a first distance in a first direction from the reference position, and then move the optical system to a second position at a second distance in a second direction from the reference position, wherein
 the second direction is opposite to the first direction with respect to the reference position, and the second distance is equal to the first distance.

2. The ophthalmologic apparatus of claim 1, further comprising an alignment indicator projector configured to project a pair of alignment indicators onto the eye, wherein
the focusing controller moves the focusing lens based on projection images of the focusing indicators captured by the fundus imaging unit after the movement of the optical system, wherein,
and
the focusing controller moves the focusing lens based on a projection image of the focusing indicators captured by the fundus imaging unit when the optical system is located in the first position, and a projection image of another of the focusing indicators captured by the fundus imaging unit when the optical system is located in the second position.

3. The ophthalmologic apparatus of claim 1, wherein
the fundus imaging unit is configured to capture a moving image of the fundus of the eye being irradiated with the light fluxes from the focusing indicator projector in parallel with the movement of the optical system by the driver, and
the focusing controller moves the focusing lens based on projection images of the focusing indicators in the moving image captured by the fundus imaging unit.

4. The ophthalmologic apparatus of claim 3, wherein
the focusing controller moves the focusing lens based on a first projection image and a second projection image rendered in the moving image, wherein
the first projection image is acquired when the optical system is located in a first direction from an initial position, and
the second projection image is acquired when the optical system is located in a second direction from the initial position.

5. The ophthalmologic apparatus of claim 4, wherein the second direction is opposite to the first direction with respect to the initial position.

6. The ophthalmologic apparatus of claim 3, further comprising an alignment indicator projector configured to project a pair of alignment indicators onto the eye, wherein
the control system controls the driver to start moving the optical system from a reference position determined based on the pair of alignment indicators.

7. The ophthalmologic apparatus of claim 1, further comprising:

an anterior eye segment imaging unit configured to capture a moving image of an anterior segment of the eye; and
a timing signal output unit configured to analyze the moving image captured by the anterior eye segment imaging unit to determine a rendering state of projection images of the light fluxes from the focusing indicator projector, and output a timing signal for capturing projection images of the focusing indicators on the fundus based on a result of the determination,
wherein the focusing controller moves the focusing lens based on projection images of the focusing indicators captured by the fundus imaging unit in response to reception of the timing signal from the timing signal output unit.

8. The ophthalmologic apparatus of claim 1, wherein the control system controls the driver to start moving the optical system to acquire projection images of the focusing indicators in response to none of the projection images of the focusing indicators being rendered in the image of the fundus captured by the fundus imaging unit.

9. The ophthalmologic apparatus of claim 1, wherein the focusing controller moves the focusing lens based on a position of the one of the projection images, and a position of another of the projection images rendered in the image of the fundus along with the movement of the optical system by the driver in response to one of projection images of the focusing indicators being rendered in the image of the fundus captured by the fundus imaging unit.

10. The ophthalmologic apparatus of claim 1, wherein the focusing controller moves the focusing lens based on a positional relationship between the projection images in response to both projection images of the focusing indicators being rendered in the image of the fundus captured by the fundus imaging unit.

11. The ophthalmologic apparatus of claim 1, further comprising a monitoring unit configured to monitor a size of a pupil of the eye,
wherein the control system controls control the driver to move the optical system to the predetermined position when the size of the pupil obtained by the monitoring unit is equal to or above a threshold.

* * * * *